United States Patent [19]

Herres

[11] Patent Number: 5,070,879
[45] Date of Patent: Dec. 10, 1991

[54] ULTRASOUND IMAGING METHOD AND APPARATUS

[75] Inventor: Bradley K. Herres, Scottsdale, Ariz.

[73] Assignee: Acoustic Imaging Technologies Corp., Phoenix, Ariz.

[21] Appl. No.: 467,335

[22] Filed: Jan. 19, 1990

Related U.S. Application Data

[63] Continuation-in-part of Ser. No. 443,752, Nov. 30, 1989, abandoned.

[51] Int. Cl.⁵ .............................................. A61B 8/00
[52] U.S. Cl. ................................ 128/660.08; 73/626; 128/662.06
[58] Field of Search ....................... 128/660.01, 660.08, 128/660.09, 660.10; 73/625, 626

[56] References Cited

U.S. PATENT DOCUMENTS

| | | | |
|---|---|---|---|
| 3,398,422 | 8/1968 | Haerten | 128/660.08 X |
| 4,186,747 | 2/1980 | Iinuma | 128/660.08 |
| 4,240,295 | 12/1980 | Uranishi | 128/660.08 X |
| 4,319,489 | 3/1982 | Yamaguchi | 73/626 |
| 4,542,746 | 9/1985 | Takamizawa | 128/660.08 X |
| 4,798,210 | 1/1989 | Ledley | 128/660.01 |
| 4,819,650 | 4/1989 | Goldstein | 128/661.01 |
| 4,932,414 | 6/1990 | Coleman | 128/660.09 |

FOREIGN PATENT DOCUMENTS

147737 7/1985 European Pat. Off. ............ 128/915
1148247 9/1989 Japan .

Primary Examiner—Francis Jaworski
Attorney, Agent, or Firm—Christie, Parker & Hale

[57] ABSTRACT

Ultrasound imaging apparatus has a probe disposed on a longitudinal axis. A linear array of ultrasound transducer elements is arranged along the axis of the probe. The array is alternatively held stationary and oscillated relative to the probe about the axis between limits to define a sector. In a first mode, the transducer elements are actuated successively while the array is held stationary to generate a longitudinal rectilinear scan. In a second mode, some of the transducer elements are actuated repeatedly while the array is oscillated to generate a transverse sector scan orthogonal to the longitudinal scan. The echoes received by the transducer elements in the first and second modes are displayed as images of respective orthogonal planes. In either case, the user selects the position of the scan plane within the field of view of the array while the probe is held in a stationary position against the skin of the patient.

18 Claims, 4 Drawing Sheets

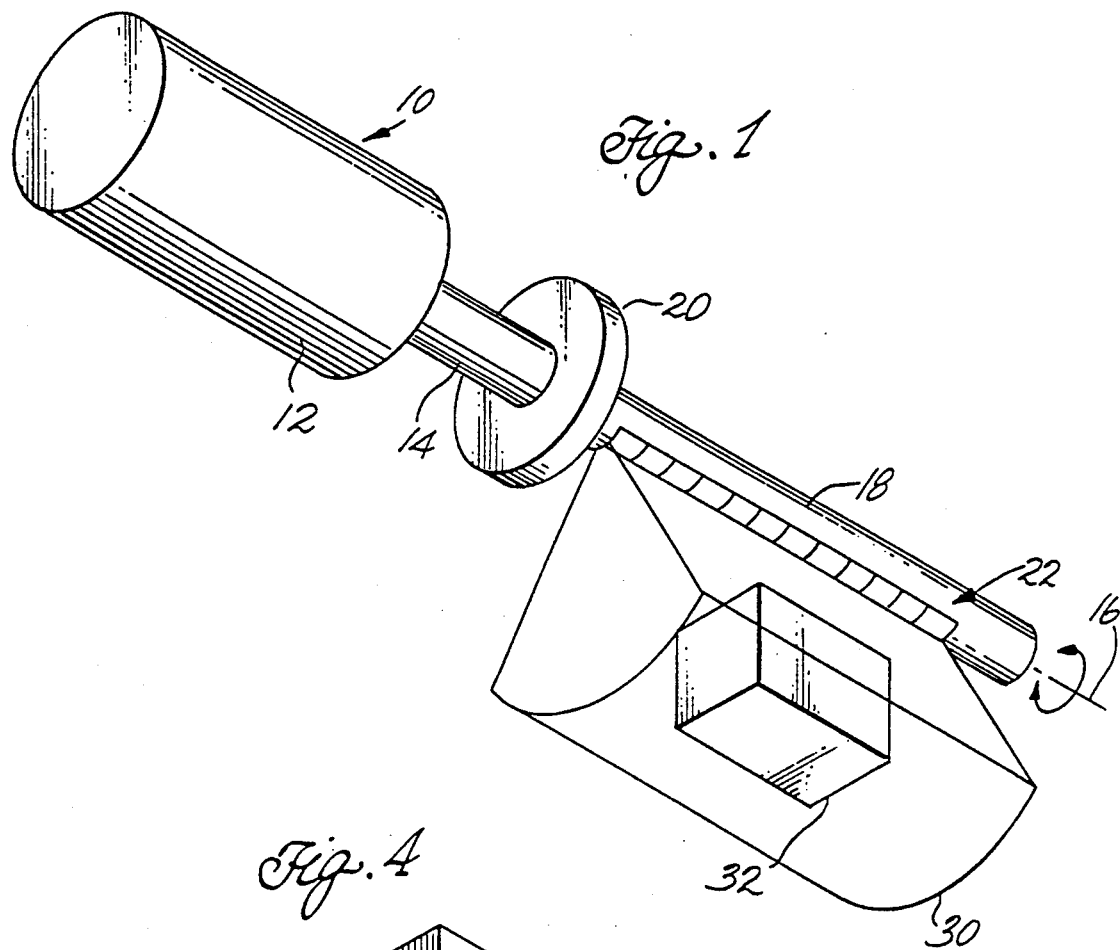
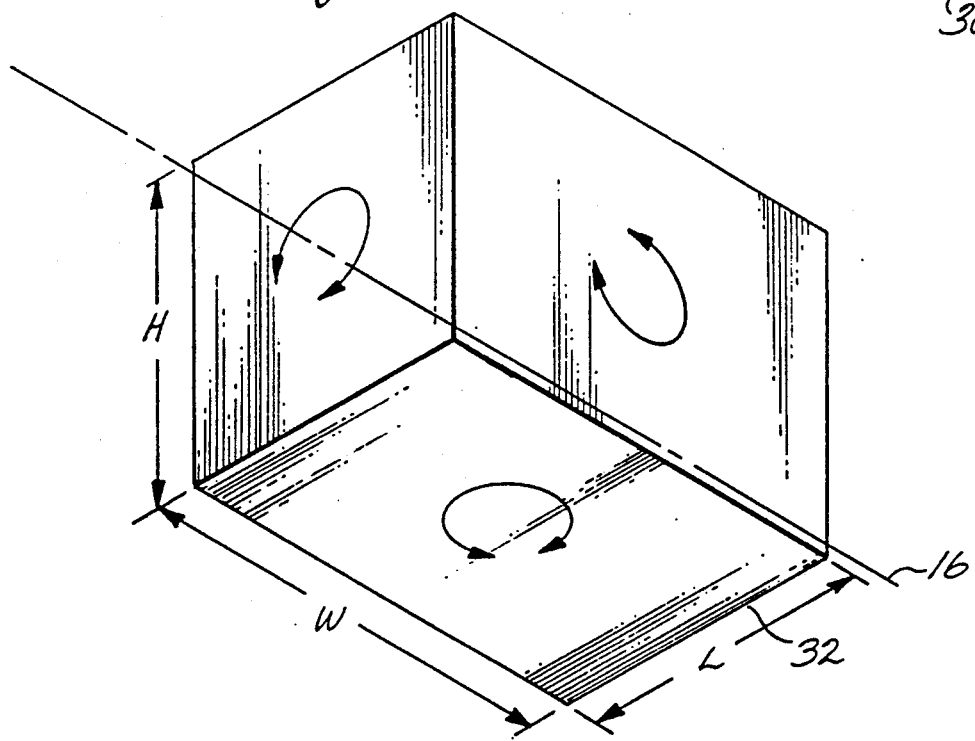

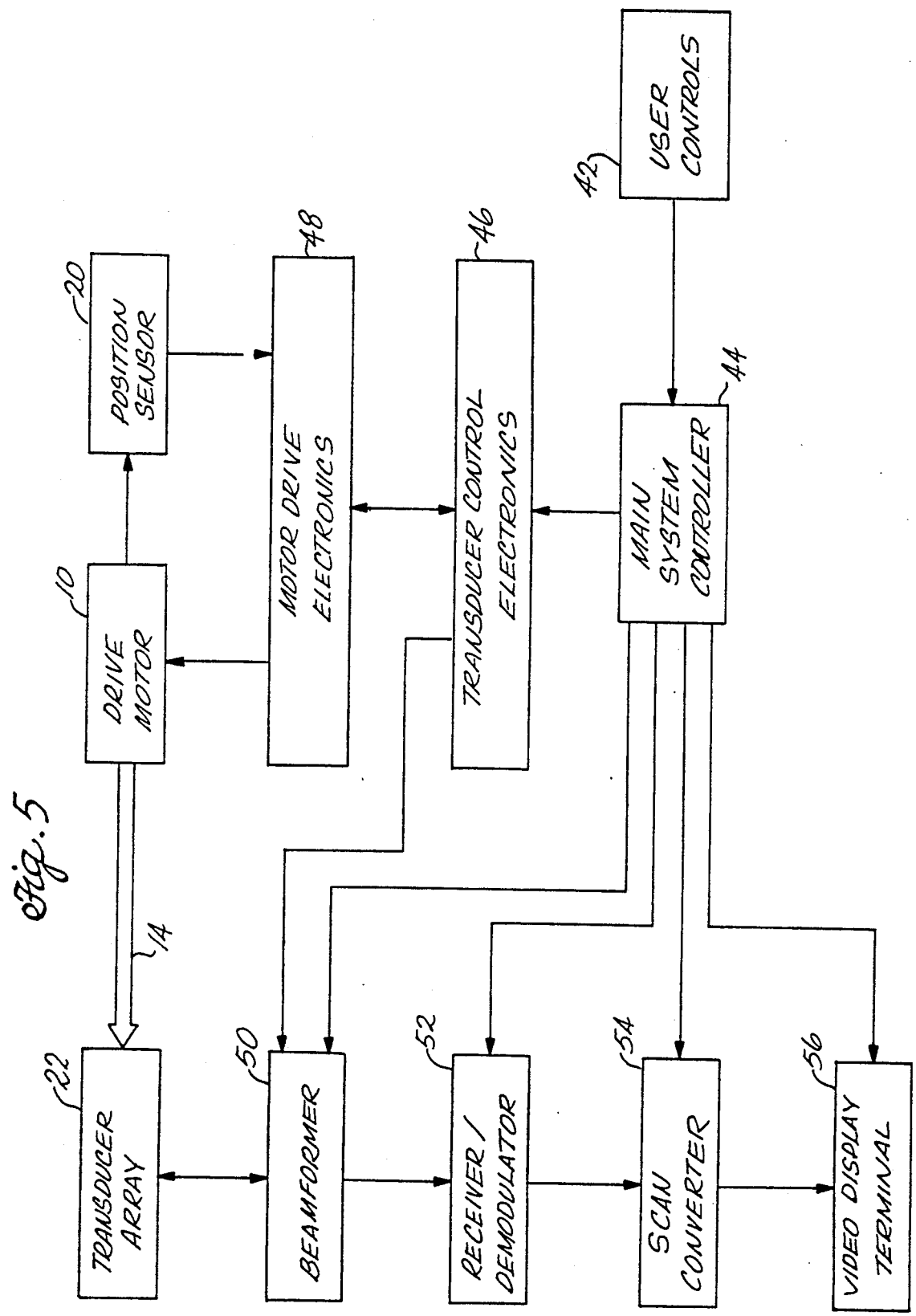

1

ULTRASOUND IMAGING METHOD AND APPARATUS

CROSS-REFERENCE TO RELATED APPLICATIONS

This is a continuation-in-part of application Ser. No. 07/443,752, field Nov. 30, 1989 and now abandoned.

BACKGROUND OF THE INVENTION

This invention relates to medical diagnostic equipment and more particularly to an ultrasound imaging method and apparatus.

Linear arrays have been used in ultrasound imaging for many years. The elements of the array are operated successively to produce parallel scan lines in a plane parallel to the length of the array. Bom U.S. Pat. No. 3,789,833, which issued on Feb. 5, 1974, discloses such a linear array.

Mechanical sector scanners have also been used in ultrasound imaging for many years. A single ultrasound element is repeatedly operated as it oscillates back and forth to produce divergent scan lines in the plane of oscillation. Examples of such mechanical sector scanners are disclosed in Finsterwald et al U.S. Pat. No. 4,426,886, which issued on Jan. 24, 1984, and Matzuk U.S. Pat. No. 4,092,867, which issued on June 6, 1978.

Ultrasound transducers that combine a linear scan and a sector scan are also known. For example, Goldstein U.S. Pat. No. 4,817,616 discloses a prostate probe that has a support member on which a pair of ultrasound transducers are mounted in longitudinally spaced relationship along an axis. One transducer is a linear array and the other transducer is a mechanical sector scanner. The transducers are oriented to scan different orthogonal planes of an object under study. A shifting mechanism moves the transducers one at a time into a unitary scanning position and actuates the transducer in the scanning position to scan the object under study.

Ledley et al. U.S. Pat. No. 4,798,210 discloses a three dimensional imaging system. In one embodiment, a plurality of ultrasound source-detectors are rotatably driven by a motor to form sector scans. As the source-detectors rotate, successive transmissions of ultrasound energy take place in directions displaced by increasing angular amounts.

SUMMARY OF THE INVENTION

According to the invention, ultrasound imaging apparatus has a probe disposed on a longitudinal axis. A linear array of ultrasound transducer elements is arranged along the axis of the probe. The array is alternatively held stationary and oscillated relative to the probe about the axis between limits to define a sector. In a first mode, the transducer elements are operated successively while the array is held stationary to generate a longitudinal rectilinear scan. In a second mode, some of the transducer elements are operated repeatedly while the array is oscillated to generate a transverse sector scan orthogonal to the longitudinal scan. The echoes received by the transducer elements in the first and second modes are displayed as images of respective orthogonal scan planes. In either case, the user selects the position of the scan plane within the field of view of the array while the probe is held in a stationary position against the skin of the patient.

It is a feature of the invention to interleave the longitudinal rectilinear scan generated by the first mode and the transverse sector scan generated by the second mode so as to permit orthogonal image planes to be displayed simultaneously.

It is another feature of the invention to operate the transducer elements in one mode repeatedly at all the transducer element positions of the other mode so as to generate a three dimensional scan. For example, transducer elements actuated in the first mode generate repeated longitudinal scans at the angular positions of the second mode to cover the entire transverse scan plane. The received echoes can be processed to display a three dimensional image from different perspectives.

BRIEF DESCRIPTION OF THE DRAWINGS

The features of specific embodiments of the best mode contemplated of carrying out the invention are illustrated in the drawings, in which:

FIG. 1 is a schematic perspective view of ultrasound imaging apparatus incorporating principles of the invention.

FIG. 4 is a diagram depicting a display screen that illustrates the display of three dimensional echo data acquired by the apparatus of FIG. 1 from an image within its field of view;

FIG. 5 is a schematic block diagram of the electronics for operating the apparatus of FIG. 1.

DETAILED DESCRIPTION OF THE SPECIFIC EMBODIMENTS

Figure 2:
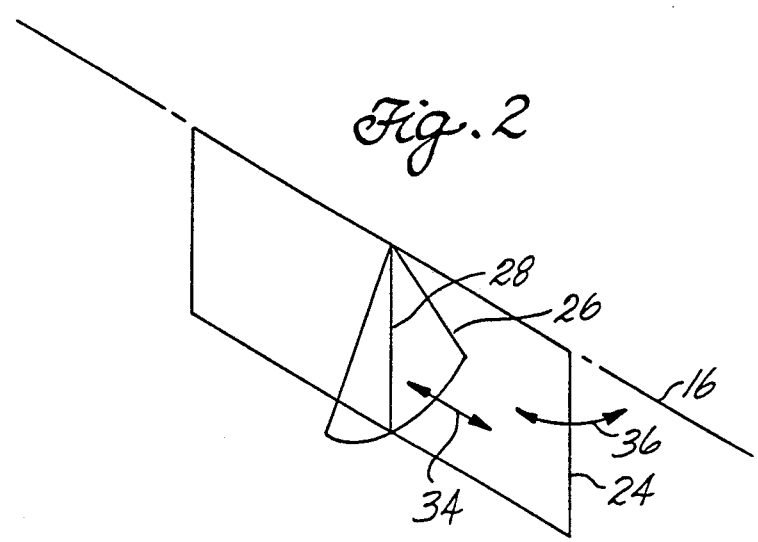
FIG. 2 is a diagram of mutually orthogonal scan planes of the apparatus of FIG. 1.

In FIG. 1 a probe has a drive motor 10 with a stationary housing 12 and a shaft 14 that oscillates back and forth in an arc about an axis 16. An axially elongated transducer holder 18 is attached to shaft 14 to rotate therewith about axis 16. A position sensor 20 is mounted on shaft 14 to generate a feedback control signal. The control signal is used to servo drive motor 10 to track a set point signal. A linear array 22 of ultrasound transducer elements is mounted on the surface of transducer holder 18 in a straight line along axis 16.

The elements of array 22 are alternatively operated in one of two modes. In the first mode, transducer holder 18 is held stationary at a selected one of a plurality of angular positions about axis 16 and the array elements are operated successively in groups of one or more elements to generate a longitudinal rectilinear scan relative to axis 16. This longitudinal scan plane is represented in FIG. 2 by reference numeral 24. In a typical example, there could be one hundred twenty eight angular positions about axis 16, there could be one hundred twenty eight array elements, and the array elements could be operated in sixty four element groups shifted successively in one element increments. For this example, sixty five parallel scan lines would le generated in the longitudinal scan plane. In the second mode, transducer holder 18 oscillates back and forth through the (e.g., one hundred twenty eight) angular positions and a selected group of the array elements are operated repeatedly at each angular position to generate a transverse sector scan relative to axis 16. This transverse scan plane is represented by reference numeral 26 in FIG. 2 and a line 28 represents the intersection of the longitudinal and transverse scan planes. In a typical example, there are one hundred twenty eight array elements, a selected group of sixty four of these elements are repeatedly operated, and there are therefore sixty five select longitudinal positions along axis 16 at which the transverse sector scan plane can be located. For this example, one hundred twenty eight diverging scan lines would be generated in the transverse scan plane. In each case, the number of elements in an operating group can be varied depending on the desired ultrasound aperture for the scan lines.

The two described modes of operation of array 22 create a field of view for transducer holder 18 that forms a cylindrical sector centered about axis 16, as depicted by reference numeral 30 in FIG. 1. A quadrilateral figure 32 having a length L, a width W, and a height H is shown in this field of view for the purpose of discussion of the capabilities of the invention. In the first mode, the user can select any of one hundred twenty eight longitudinal scan planes within field of view 30. In the second mode, the user can select any of sixty four transverse scan planes within field of view 30.

Figure 3:
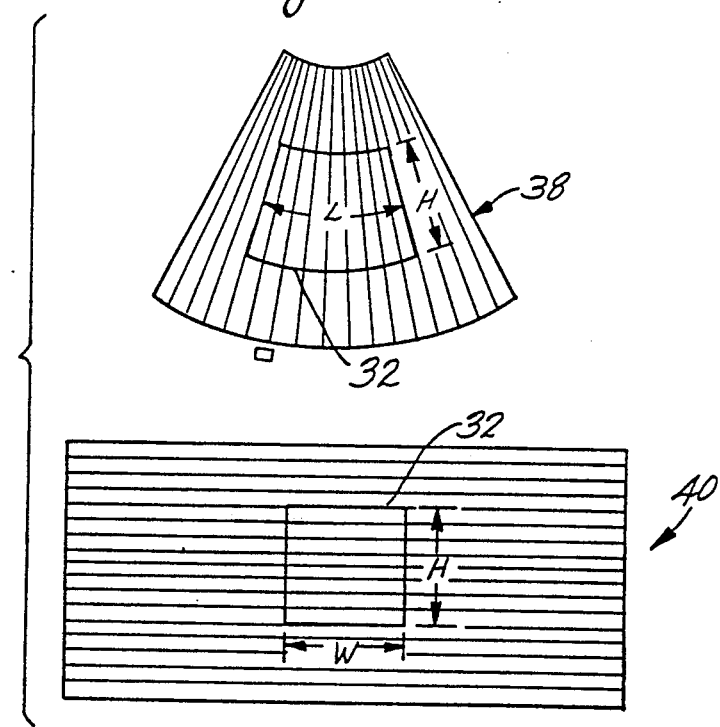
FIG. 3 is a diagram depicting a display screen that illustrates the simultaneous display of echo data acquired by the apparatus of FIG. 1 from an image in the scan planes of FIG. 2.

By combining the two modes, the user can acquire and display echo data in orthogonal B-scan planes at the same time (FIG. 2), varying the location of either or both of the scan planes within field of view 30, as represented by arrows 34 and 36 (FIG. 2), to examine different regions thereof in real time while the probe remains in a stationary position in contact with the patient's skin. In one combined mode, transducer holder 18 oscillates back and forth to generate the transverse B-scan, but stops momentarily each time the angular position of the selected longitudinal scan plane is reached to successively operate the elements once end then again continues to oscillate. This produces transverse and longitudinal B-scans at the same frame rate. If a higher frame rate is desired for the transverse scan, transducer holder 18 would only stop every other, every second, or other fraction of the cycle of oscillations of transducer holder 18. In another combined mode, the array elements operate successively with transducer holder 18 held stationary to generate the longitudinal scan, but momentarily stop operating successively each time the longitudinal position of the selected transverse scan plane is reached to operate the corresponding group of elements repeatedly while oscillating transducer holder 18 once and then again continue to operate successively with transducer holder 18 held stationary. This produces transverse and longitudinal B-scans at the same frame rate. If a higher frame rate is desired for the longitudinal scan, transducer holder 18 would only oscillate every other, every second, or o&her fraction of the cycle of successive operation. FIG. 3 depicts the screen of a video display terminal that simultaneously displays the height H and the length L of FIG. 32 in a transverse sector B-scan 38 and the height H and the width W of FIG. 32 in a longitudinal rectilinear B-scan 40. The diverging lines of scan 38 represent the scan lines of the transverse scan, and the parallel lines of scan 40 represent the scan lines of the longitudinal scan.

By combining the two B-scan modes, the user can also acquire and display echo data in three dimensions. Preferably, the three-dimensional data is acquired by operating array 22 in the first mode at each angular position of holder 18, thereby generating a longitudinal scan at each such angular position. In this way, only one oscillation of holder 18 is required to make a complete three dimension scan of the field of view. Whether holder 18 remains stationary or is moving toward the next angular position during each operation of array 22 in the first mode is a trade off of speed versus image quality. If holder 18 is held stationary, fewer artifacts are formed and the image quality is improved. If holder 18 is moving, a higher speed and therefor scan rate can be realized. There are in existence computer programs that process and display three dimensional image data so that the acquired image can be rotated about three mutually orthogonal axes for viewing of all its aspects. As illustrated in FIG. 4, use of such programs with the invention permits FIG. 32 to be rotated on the screen of a video display terminal to view all aspects of FIG. 32.

In FIG. 5 is shown the electronics for operating the apparatus of FIG. 1. As described above in connection with FIG. 1, shaft 14 of drive motor 10 is connected to transducer holder 18 and thus oscillates array 22 back and forth about axis 16 when motor 10 is operating. Position sensor is also connected to shaft 14 to generate a signal proportional to the angular position of shaft 14 about axis 16. Responsive to signals from user controls 42 that are representative of selected operating parameters, a main system controller 44 computes a time varying set point signal representative of the desired angular position of shaft 14 as a function of time. The set point signal is coupled to transducer control electronics 46 and to motor drive electronics 48. Responsive to the position sensor signal and the set point signal, motor drive electronics 48 operates drive motor 10 so shaft 14 tracks the angular shaft position set point. Coordinated with the set point signal and the user control signals, transducer control electronics 46 selects the groups of elements of array 22 to be operated as a function of time. Main system controller 44 performs the timing functions to acquire and display the echo data. A beam former 50 includes conventional electronics to select groups of array elements for transmission and reception responsive to transducer control electronics 46 and to focus the beam, if desired, responsive to main system controller 44. Beam former 50 controls the application of excitation pulses to the selected groups of the elements of array 22. The echo signals intercepted by the selected groups of array elements are coupled by beam former 50 to a conventional receiver/demodulator 52. Main system controller adjusts the operating parameters of receiver/demodulator 52 in accordance with well known techniques. The video signal processed by receiver/demodulator 52 is coupled to a conventional scan converter 54, in which the storage and retrieval of the echo data is coordinated by main system controller 44. The echo data is coupled from scan converter 54 to a video display terminal 56 under the control of main system controller 44.

Figure 6:
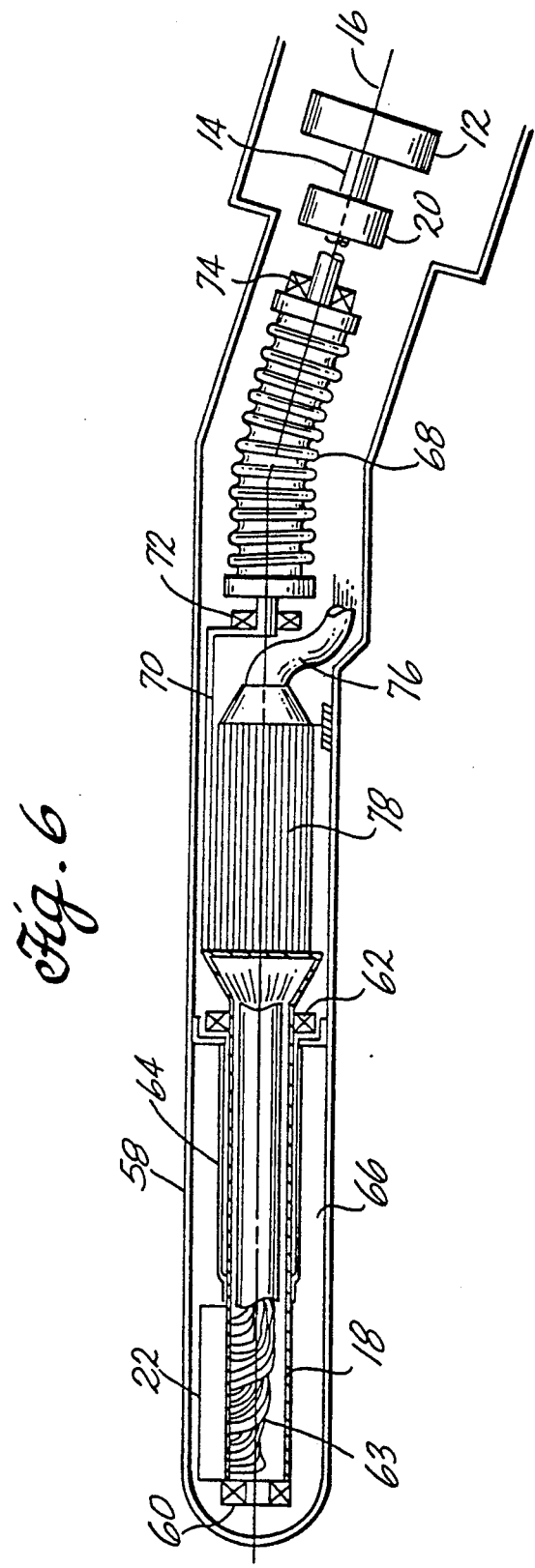
FIG. 6 is a side sectional view of a transrectal probe that incorporates the apparatus of FIG. 1.

In FIG. 6, a transrectal probe has an elongated housing 58 shaped to fit into the rectal cavity. Inside housing 58, transducer holder 18, which is hollow, is journalled for rotation about axis 16 between stops (not shown) by bearing 60 and 62. Array 22 is mounted at the distal end of transducer holder 48 parallel to axis 16. A plurality of array element leads 63 pass through transducer holder 48 from array 22 to the other end. A stationary elastoxeric sheath 64 fits snugly around the remainder of transducer holder 48 and is secured to the inner wall of housing 58 adjacent to bearing 62 to define a sealed fluid chamber 66. An acoustic coupling fluid fills chamber 66. The portion of housing 58 forming the outer boundary of chamber 66 is acoustically transparent because ultrasound energy passes therethrough in operation. A flexible shaft 68, such as a bellows coupler, connects shaft 14 of motor 12 to a rigid off center shaft 70. Shaft 68 is journalled for rotation by bearings 72 and 74. By way of example, position sensor 14 could be a rotational variable differential transformer. Shaft 70 is secured to transducer holder 48 so the latter is driven by motor 12 via shafts 14, 68, and 70. A stationary cable 76 leads to the electronics described above in connection with FIG. 5. A flex connector 78 forms the electrical and mechanical connection between leads 63 and the leads of cable 76. In the manner described above, the user can select one of a number of longitudinal scan planes and/or one of a number of transverse scan planes for individual or simultaneous viewing on the video display terminal without moving the probe in the rectal cavity. Alternatively, the user can select three dimensional acquisition of all the echoes in the cylindrical seztoral field of view for display as a rotating three dimensional image.

The described embodiment of the invention is only considered to be preferred and illustrative of the inventive concept; the scope of the invention is not to be restricted to such embodiments. Various and numerous other arrangements may be devised by one skilled in the art without departing from the spirit and scope of this invention. For example, instead of a straight linear array, a convexly curved linear array could be used, in which case a longitudinal sector scan is generated. Or the drive motor could be located beside the transducer holder rather that in line therewith, depending on the shape of the probe housing.

What is claimed is:

1. Ultrasound imaging apparatus comprising:
   a probe having a longitudinal axis;
   a linear array of ultrasound transducer elements arranged along the axis of the probe;
   drive means for alternatively holding the array stationary and oscillating the array relative to the probe about the axis between limits to define a sector;
   means in a first mode for operating the transducer elements successivley while the drive means holds the array stationary to generate a longitudinal scan;
   means in a second mode for operating some transducer elements repeatedly while the drive means oscillates the array to generate a transverse scan;
   means in the first mode for selecting the angle about the axis at which the array is held stationary for successive operation to control the longitudinal scan plane about the axis; and
   means for displaying the echos received by the transducer elements in the first and second modes.

2. The apparatus of claim 1, additionally comprising:
   means in the second mode for selecting one or more adjacent transducer elements for repeated operation to control the transverse scan plane along the axis.

3. A method for using a linear array of ultrasound transducer elements arranged along an axis, the method comprising the steps of:
   alternatively holding the array stationary and oscillating the array relative about the axis between limits to define a sector;
   operating the transducer elements successively in a first mode while the array is being held stationary to generate a longitudinal B-scan;
   operating some of the transducer elements repeatedly in a second mode while the array is being oscillated to generate a transverse B-scan; and
   simultaneously displaying the longitudinal B-scan and the transverse B-scan echos received by the transducer elements in the first and second modes.

4. The method of claim 3, additionally comprising the step of selecting the angle about the axis at which the angle is held stationary in the first mode for successive operation to control the longitudinal scan plan about the axis.

5. The method of claim 3, additionally comprising the step of selecting one or more adjacent transducer elements in the second mode for repeated operation to control the transverse scan plan along the axis.

6. Ultrasound imaging apparatus comprising:
   a probe having a longitudinal axis;
   a linear array of ultrasound transducer elements arranged along the axis of the probe;
   drive means for alternatively holding the array stationary and oscillating the array relative to the probe about the axis between limits to define a sector;
   means in a first mode for operating the transducer elements successively while the drive means holds the array stationary to generate a longitudinal scan;
   means in a second mode for operating some transducer elements repeatedly while the drive means oscillates the array to generate a transverse scan;
   means in the second mode for selecting one or more adjacent transducer elements for repeated operation to control the transverse scan plane along the axis; and
   means for displaying the echos received by the transducer elements in the first and second modes.

7. Ultrasound imaging apparatus comprising:
   a probe having a longitudinal axis;
   a linear array of ultrasound transducer elements arranged along the axis of the probe;
   drive means for alternatively holding the array stationary and oscillating the array relative to the probe about the axis between limits to define a sector;
   means in a first mode for operating the transducer elements successively while the drive means holds the array stationary to generate a longitudinal scan;
   means in a second mode for operating some transducer elements repeatedly while the drive means oscillates the array to generate a transverse scan;
   means in a third mode for operating a group of fewer than all the transducer elements repeatedly while the drive means oscillates the array to generate a transverse scan, interrupting each oscillation at a selected angle about the axis, and operating the transducer elements successively during each interruption to generate a longitudinal scan at the selected angle; and
   means for displaying the echos received by the transducer elements in the first and second modes.

8. The apparatus of claim 7, additionally comprising:
   means in a fourth mode for operating the transducer elements successively while the drive means holds the array stationary to generate a longitudinal scan, oscillating the array each succession at a selected array position along the axis, and operating the transducer elements repeatedly during each oscillation to generate a transverse scan at the selected array position.

9. The apparatus of claim 7, in which the displaying means simultaneously displays the echos from the transverse scan and the longitudinal scan.

10. Ultrasound imaging apparatus comprising:
a probe having a longitudinal axis;
a linear array of ultrasound transducer elements arranged along the axis of the probe;
drive means for alternatively holding the array stationary and oscillating the array relative to the probe about the axis between limits to define a sector;
means in a first mode for operating the transducer elements successively while the drive means holds the array stationary to generate a longitudinal scan;
means in a second mode for operating some transducer elements repeatedly while the drive means oscillates the array to generate a transverse scan;
means in a third mode for operating a group of fewer than all the transducer elements repeatedly while the drive means oscillates the array to generate a transverse scan, interrupting each oscillation at a selected angle about the axis, and operating the transducer elements successively during the interruption to generate a longitudinal scan at the selected angle; and
means for displaying the echos received by the transducer elements in the first and second modes.

11. The apparatus of claim 10, in which the displaying means simultaneously displays the echos from the transverse scan and the longitudinal scan.

12. Ultrasound imaging apparatus comprising:
a probe having a longitudinal axis;
a linear array of ultrasound transducer elements arranged along the axis of the probe;
drive means for alternatively holding the array stationary and oscillating the array relative to the probe about the axis between limits to define a sector;
means in a first mode for operating the transducer elements successively while the drive means holds the array stationary to generate a longitudinal scan;
means in a second mode for operating some transducer elements repeatedly while the drive means oscillates the array to generate a transverse scan;
means in a third mode for operating successive groups of fewer than all the transducer elements repeatedly while the drive means oscillates the array to generate successive transverse scans at the transducer element positions along the axis; and
means for displaying the echos received by the transducer elements in the first and second modes.

13. The apparatus of claim 12, in which the displaying means simultaneously displays the echos from the scans in three dimensions.

14. Ultrasound imaging apparatus comprising:
a probe having a longitudinal axis;
a linear array of ultrasound transducer elements arranged along the axis of the probe;
drive means for alternatively holding the array stationary and oscillating the array relative to the probe about the axis between limits to define a sector;
means in a first mode for operating the transducer elements successively while the drive means holds the array stationary to generate a longitudinal scan;
means in a second mode for operating some transducer elements repeatedly while the drive means oscillates the array to generate a transverse scan;
means in a third mode for incrementally oscillating the array to the angular positions about the axis and operating the transducer elements successively while holding the array stationary at the angular positions to generate incremental longitudinal scans at the angular positions about the axis; and
means for displaying the echos received by the transducer elements in the first and second modes.

15. The apparatus of claim 14, in which the displaying means simultaneously displays the echos from the scans in three dimensions.

16. Ultrasound imaging apparatus comprising:
a probe having a longitudinal axis;
a linear array of ultrasound transducer elements arranged along the axis of the probe;
drive means for alternatively holding the array stationary and oscillating the array relative to the probe about the axis between limits to define a sector;
means in a first mode for operating the transducer elements successively while the drive means holds the array stationary to generate a longitudinal B-scan;
means in a second mode for operating some transducer elements repeatedly while the drive means oscillates the array to generate a transverse B-scan; and
means for simultaneously displaying the longitudinal B-scan and transverse B-scan echos received by the transducer elements in the first and second modes.

17. The apparatus of claim 16, in which the ultrasound transducer elements are arranged in a straight line along the axis of the probe.

18. Ultrasound imaging apparatus comprising:
a probe having a longitudinal axis;
a linear array of ultrasound transducer elements rotatably mounted on the probe in a straight line along its axis;
drive means for oscillating the array relative to the probe about the axis between limits to define a cylindrical sectorial field of view;
means for operating the transducer elements successively to generate a plurality of longitudinal scans covering the field of view; and
means for displaying the echos received by the transducer elements in three dimensions.

* * * * *